US00PP11122P

United States Patent [19]

Bovio

[11] Patent Number: Plant 11,122

[45] Date of Patent: Nov. 16, 1999

[54] LAMIUM PLANT NAMED 'ORCHID FROST'

[76] Inventor: Michael A. Bovio, 6250 Hickory Meadows Dr., White Lake, Mich. 48383

[21] Appl. No.: 09/038,578

[22] Filed: Mar. 11, 1998

[51] Int. Cl.[6] ..... A01H 5/00

[52] U.S. Cl. ..... Plt./263

[58] Field of Search ..... Plt./263

*Primary Examiner*—Howard J. Locker

*Assistant Examiner*—Wendy A Baker

[57] ABSTRACT

A *Lamium maculatum* plant named 'Orchid Frost', characterized by its violet flowers and vigorous growth habit in addition to its colorful silvery centered, green-edged foliage.

6 Drawing Sheets

The present invention comprises a new and distinct cultivar of *Lamium maculatum,* hereafter referred to by the cultivar name 'Orchid Frost'.

'Orchid Frost' is a new and distinct variety of spotted dead nettle, an herbaceous perennial from Europe. 'Orchid Frost' is unique and outstanding for its violet flowers and vigorous growth habit. It is characterized in addition by its colorful silvery centered, green-edged foliage.

'Orchid Frost' originated as a chance seedling of unknown parentage. The first successful asexual reproduction of 'Orchid Frost' was carried out by its discoverer, Mike Bovio. This propagation took place under controlled conditions at Howell, Mich., on May 24, 1996. The plant has maintained the same characteristics through successive asexual propagations.

The sport was excised, the bottom leaves removed, treated with IBA, and rooted under intermittent mist over the period of two weeks. Three cuttings rooted and were transplanted for evaluation.

'Orchid Frost' has not been observed under all possible environmental conditions, and the phenotype may vary significantly with variations in environment, such as temperature, light intensity and day length. The following observations, measurements, and comparisons describe this plant as grown in White Lake, Mich. when container grown (outdoors without cover) in conditions that approximate those generally used in commercial practice.

BRIEF DESCRIPTION OF THE DRAWINGS

The accompanying photographic illustrations show typical foliage of the cultivar and the closest known comparison cultivars, with color being as accurate as possible with renditions of this type. The photographs were taken at 4 P.M. on Sep. 28, 1997 under partly sunny conditions, in White Lake, Mich. The film used was Kodak Gold ISO 200 exposed for 1/500 second at F4 using no filters with one exception—illustration 5 was taken with Fujicolor 100 ISO at 1/250 second at F4 under with overcast sky using no filter.

Figure 1:
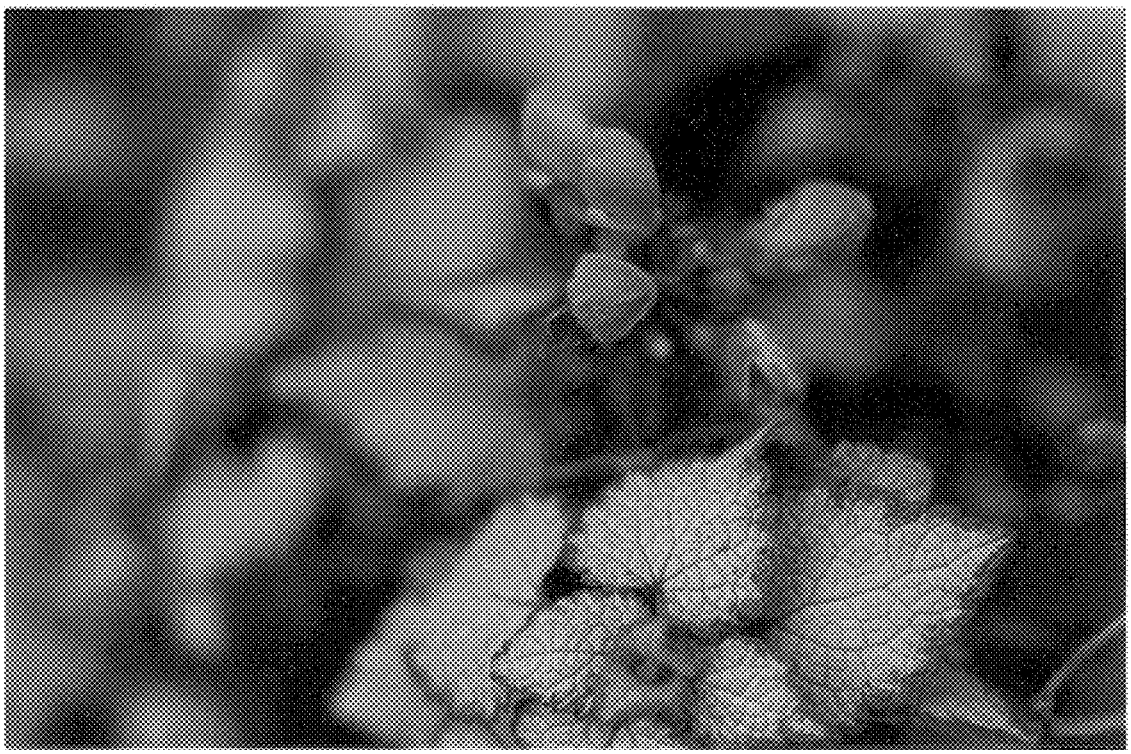
FIG. 1 and FIG. 2 are perspective views of 'Orchid Frost'.
Figure 2:
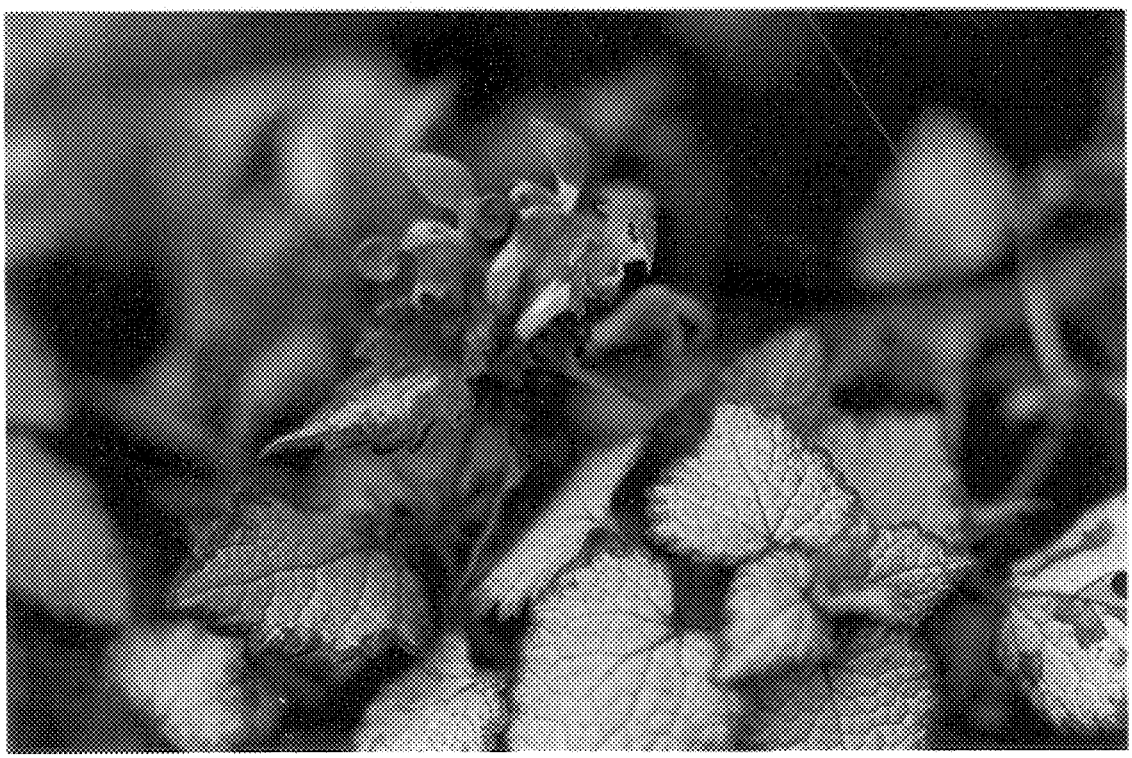
Figure 3:
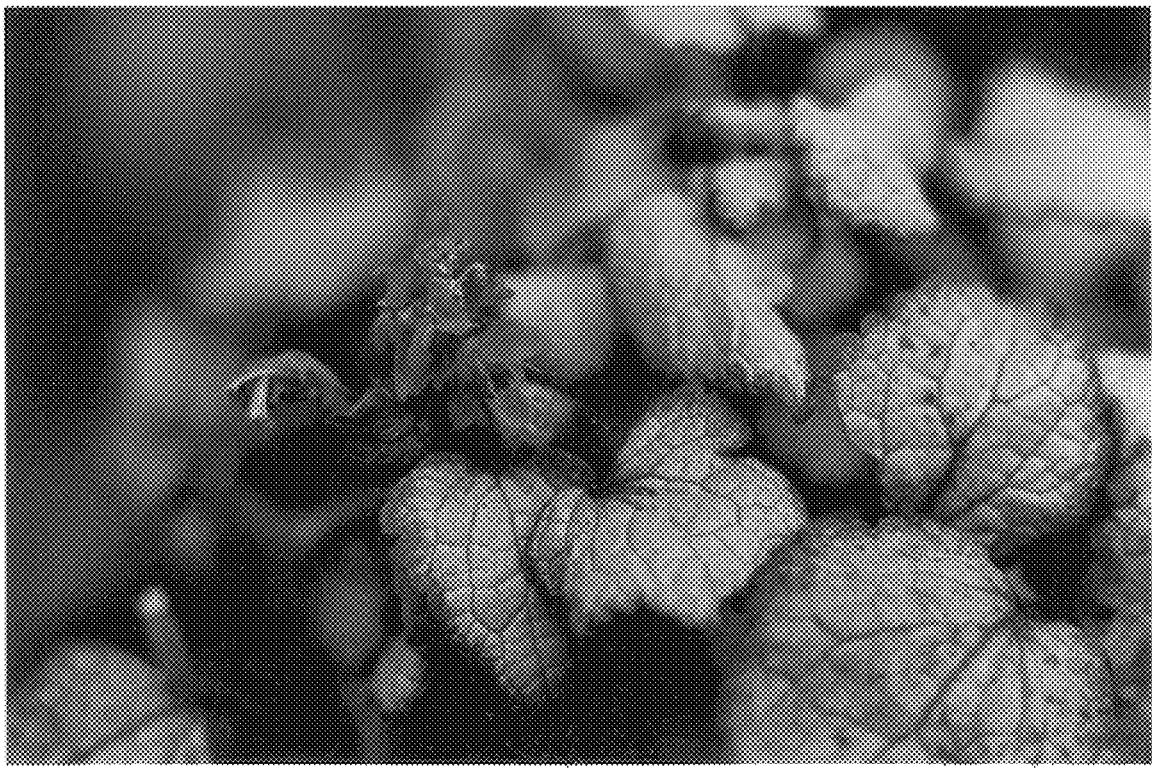
FIG. 3 and FIG. 4 are perspective views of *L. maculatum* 'Beacon Silver'.
Figure 4:
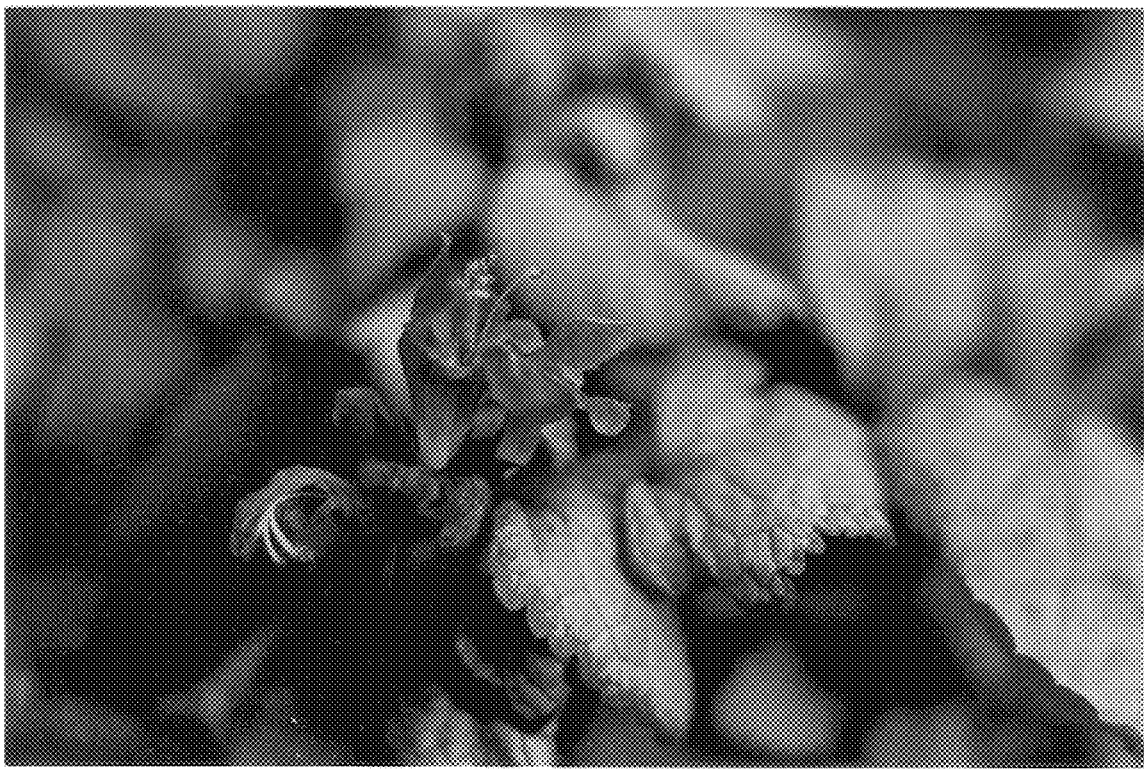
Figure 5:
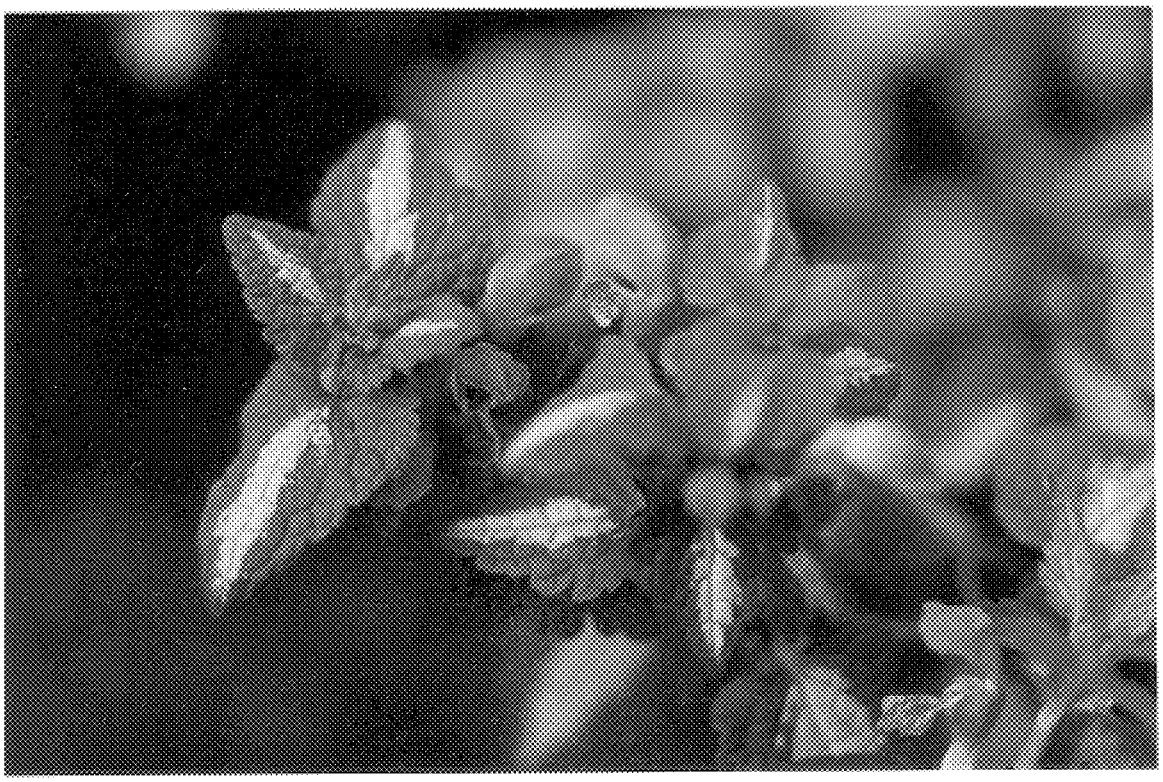
FIG. 5 and FIG. 6 are perspective views of *L. maculatum* 'Chequers'.
Figure 6:
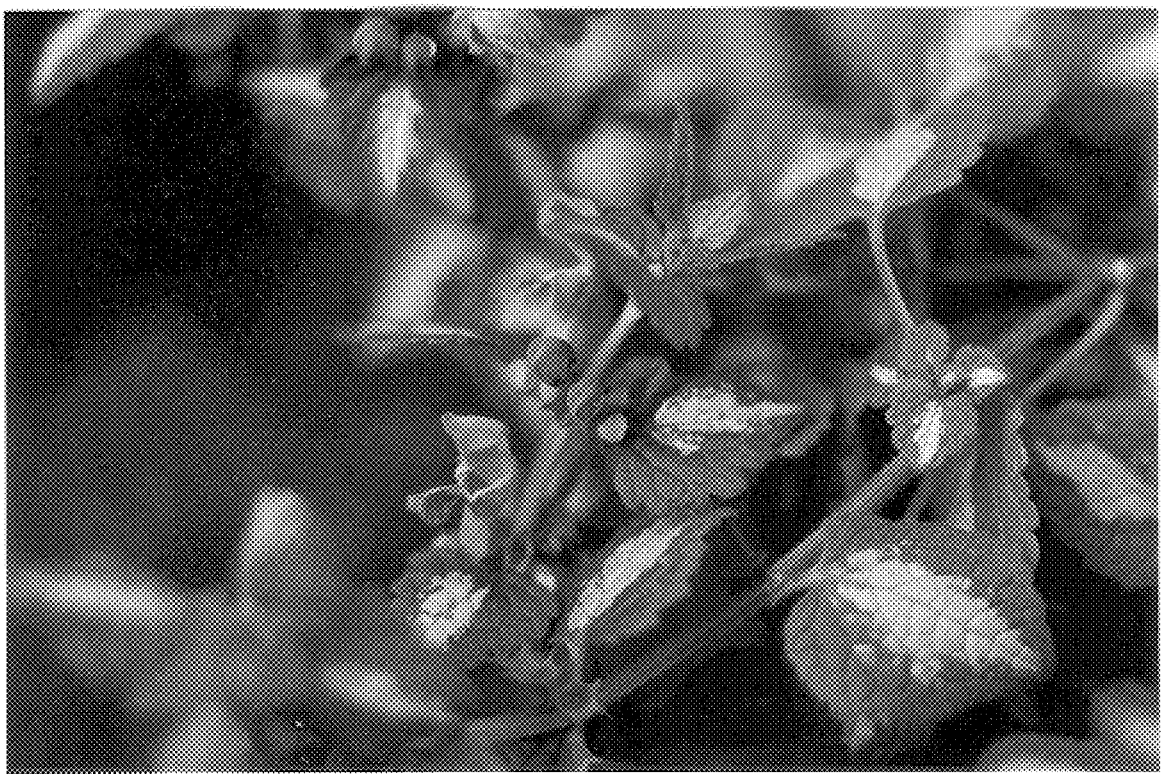
Figure 7:
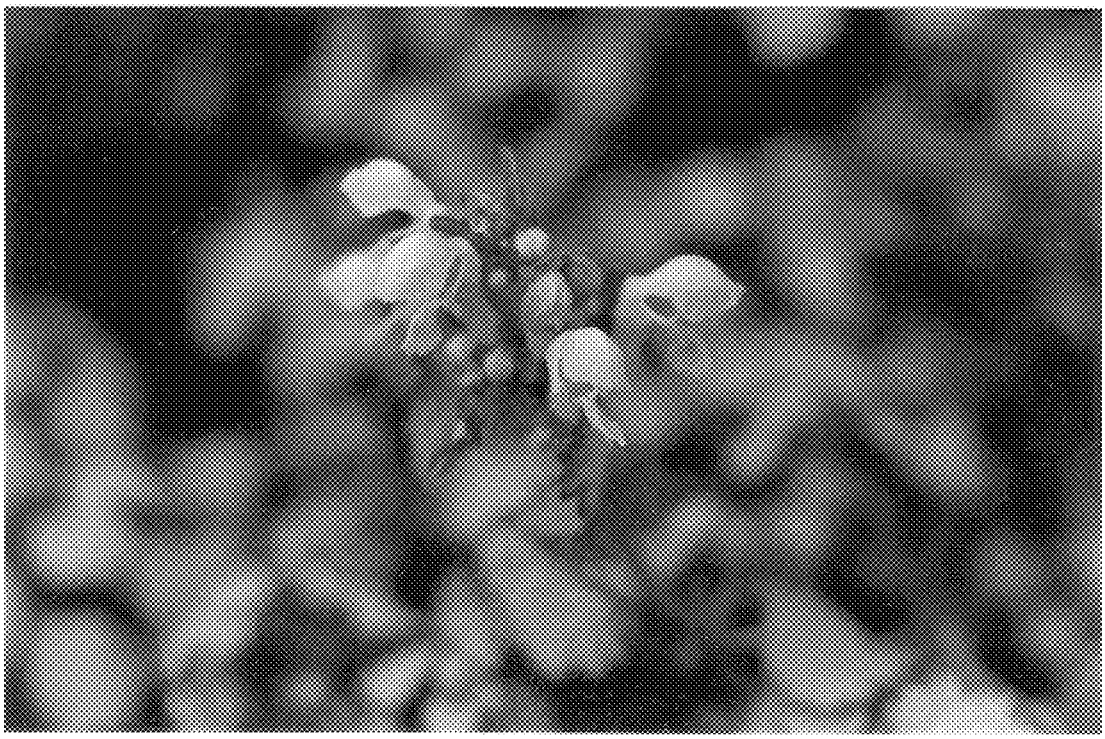
FIG. 7 is a perspective view of *L. maculatum* 'Pink Pewter'.
Figure 8:
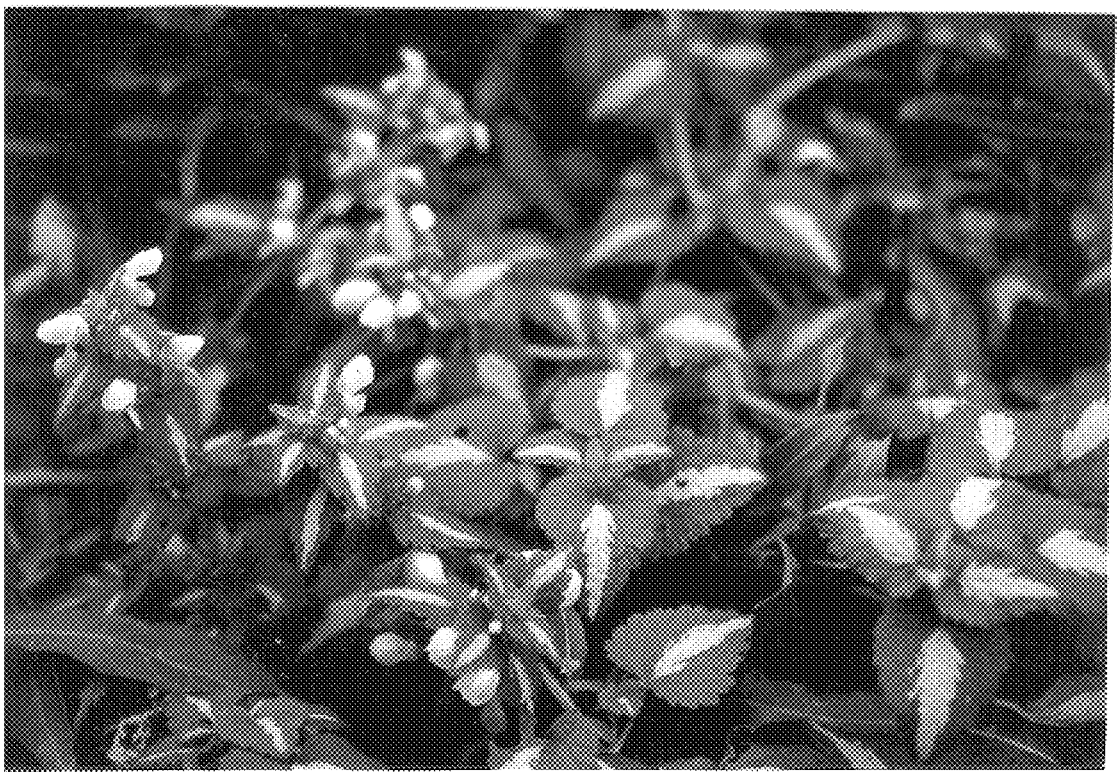
FIG. 8 is a perspective view of *L. maculatum* 'Shell Pink'.
Figure 9:
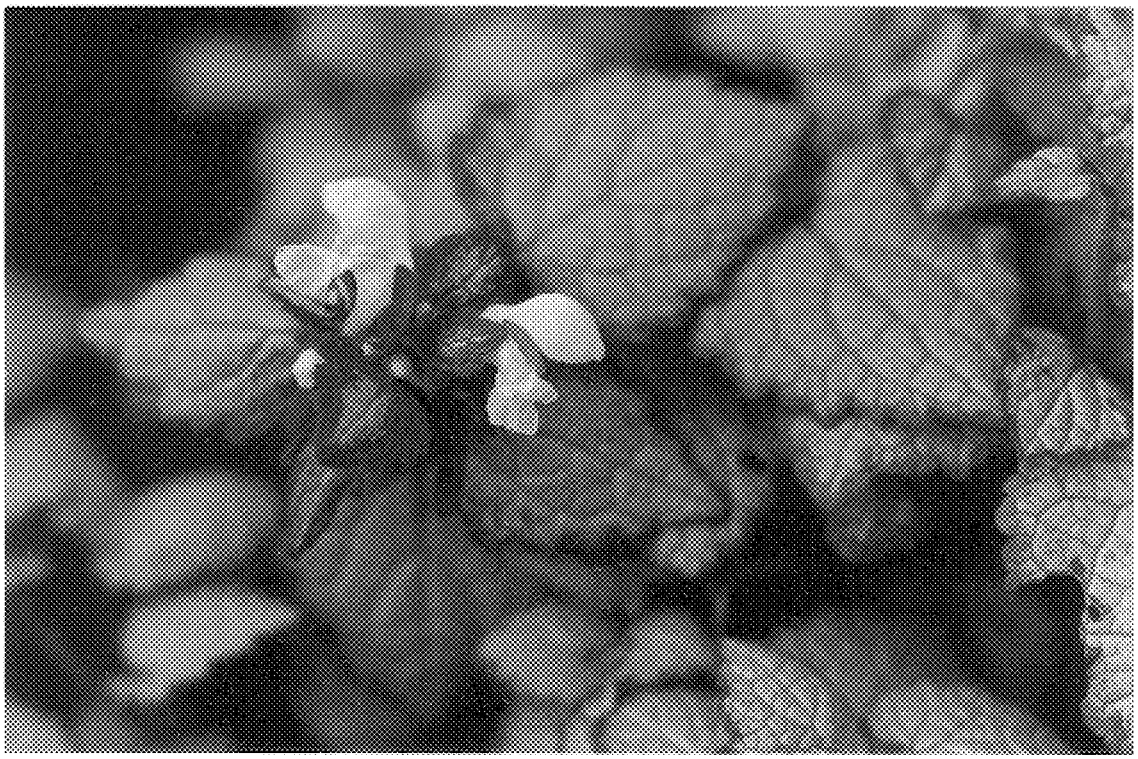
FIG. 9 and FIG. 10 are perspective views of *L. maculatum* 'White Nancy', and FIG. 11 and FIG. 12 feature 'Orchid Frost' with the two most similar cultivars 'Pink Pewter' and 'Beacon Silver'.
Figure 10:
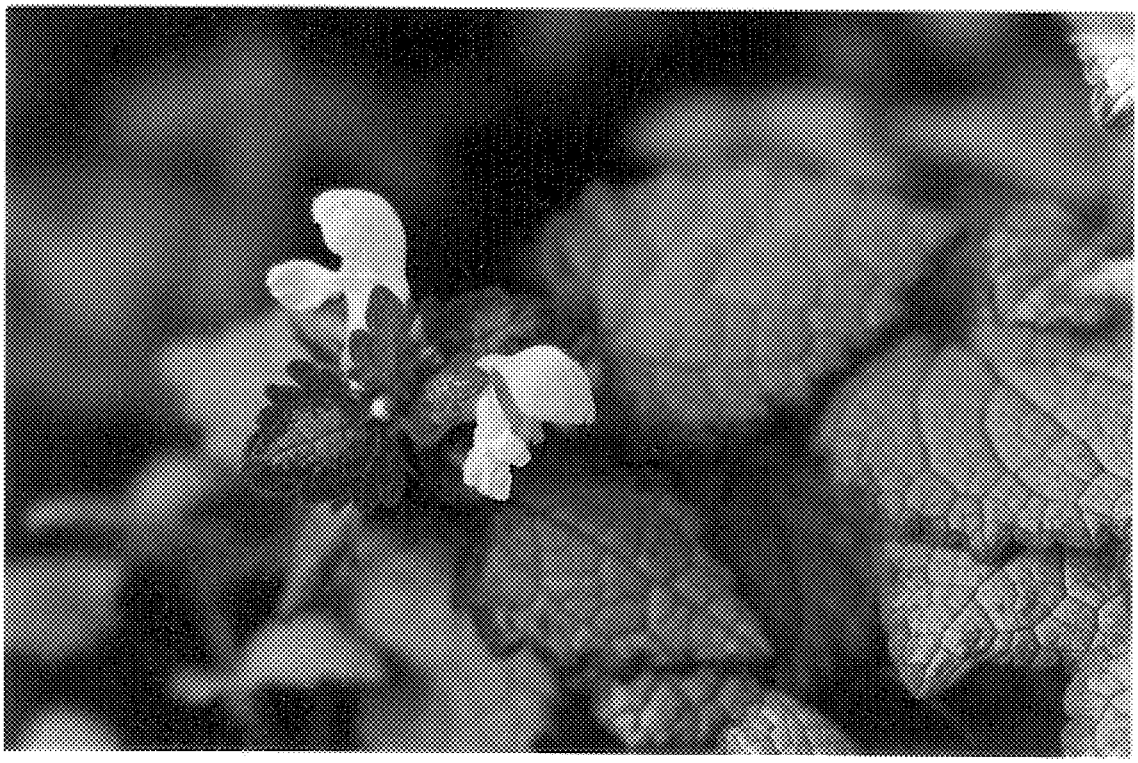
Figure 11:
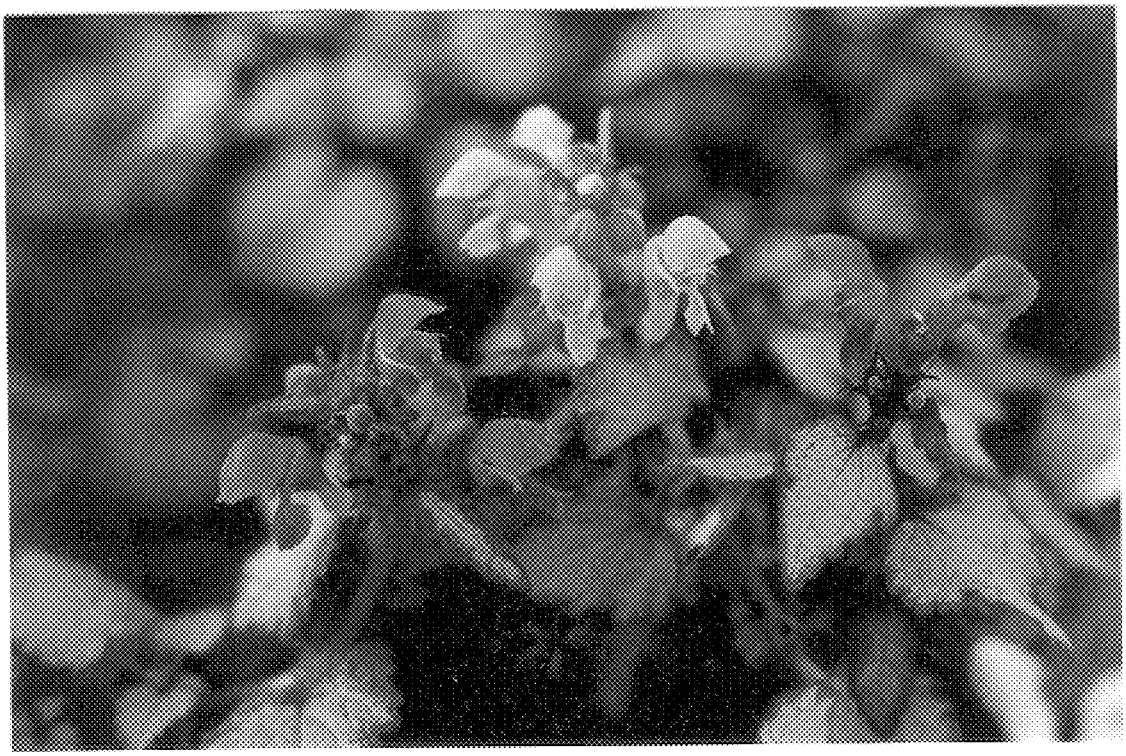
Figure 12:
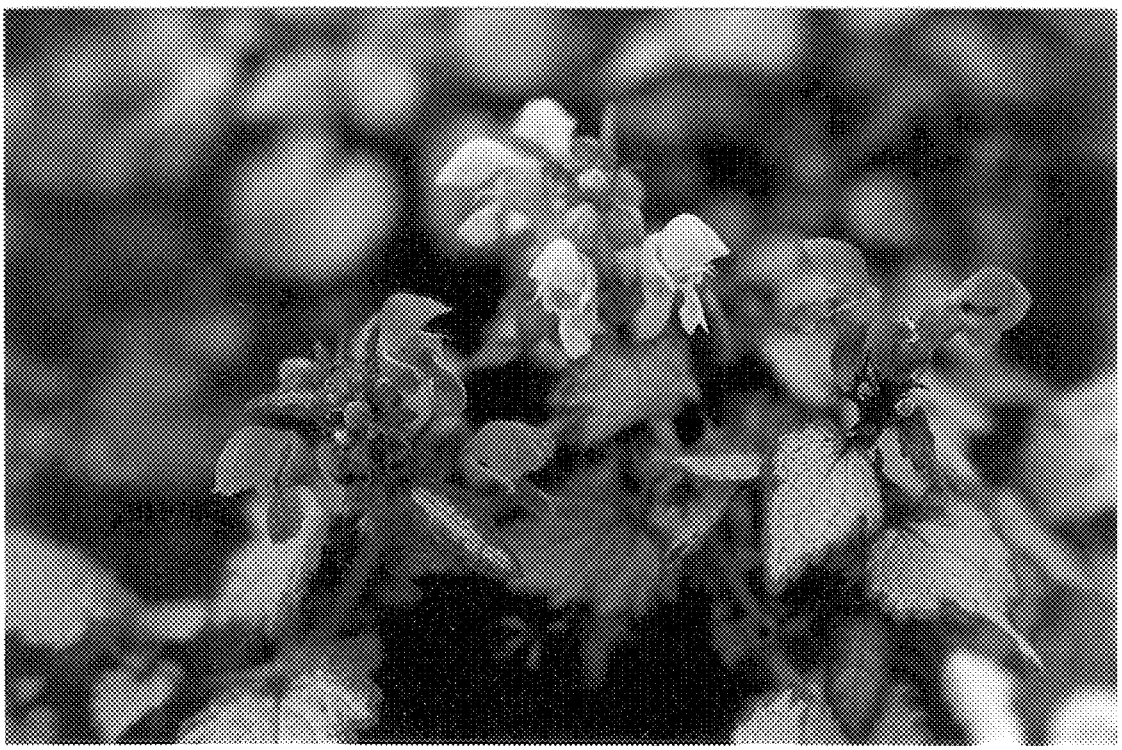

The following traits have been repeatedly observed and are determined to be the basic characteristics of Orchid Frost, which in combination distinguish this dead nettle as a new and distinct cultivar. The color codes correspond to The Royal Horticultural Society Colour Chart.

1. Stems of this cultivar arise at acute angles to the growing medium. As they elongate their weight causes them to droop over and sprawl horizontally—usually contacting the growing medium. Typically they reach 12 or more inches in length and often produce branches at their nodes.

2. Typical stems are herbaceous and are uniformly colored light green 135-D. The stems are square in cross section and 3/16 inch in diameter.

3. Internodes range in length from ½ to 2 inches. The nodes are the same dimensions as the internodes and often sprout roots after a few weeks of contact with the growing medium. Thereafter, the plants generate a pair of new shoots from the buds on the distal end of the nodes.

4. Evergreen foliage is simple and arranged in opposite pairs. In youth, the foliage is ovate in outline, crenate edged, and colored either light green 145-A (about 25 percent of the new leaves are colored this way), or bicolored with the same coloration as the mature leaves (see # 5 below).

5. Mature leaves are cordate, crenate or crentate-dentate margined. Ranging from 1½–2 inches long by 1¼ to 1½ inches wide, they are attached by ¾–1 inch long light green petioles 135-D. Hair covered, they are somewhat velvety to the touch. Each is flat, with obtuse apices.

6. The midribs are not prominent and are only slightly recessed into the blade. Colored medium green 143-A, they give rise to a network of secondary and terciary veins of the same color.

7. Adult leaves are bicolored. The center is colored gray-green 192-C, and the leaf edge green 143-A. The leaf edge surrounds the entire leaf blade and is typically ⅛ inch wide. Plant height is typically 4 inches, mounding to 8 inches.

8. Bisexual flowers are arranged in verticillasters (dense whorls) and are borne primarily during late spring and early summer then the plant exhibits a lighter re-blooming in the late summer and fall months. Each whorl may produce up to 20 flowers, but not all at the same time.

9. Individual flowers are bilabiate (typical of the mint family). The flowers are typically borne in multiples of five, with medium green 143-A, linear, divergent, lobed calyxes. Each corolla is approximately 1 inch long by 7/16 inch wide, two-lipped, upper lip hooded, lower lip 3-lobed.

10. The funnel-like base of each corolla is colored white 155-D. The upper lip is violet 84-C on the inside and violet 84-A on its outside. The lateral lower lips are colored violet 84-A on their outsides and white 155-B on their insides. The central lower lip is colored violet 83-D on both sides. The width of the corolla is typically ⅜ inch across.

11. The fruit, grouped in fours, is unnoticable with casual observation. Each is a tiny ⅛ inch long, 1/16 inch wide, green 135-D nutlet.

Other registered and related cultivars of spotted dead nettle are:

'Beacon Silver', a less vigorous, more disease prone selection with flowers somewhat smaller ¾ inch long by 7/16 inch wide, colored red-purple 186-C on the outside of the upper lip of the corolla, and leaves with similar variegation and coloring (to 'Orchid Frost') but smaller, 1⅜ inch long by 1¼ inch wide, often irregularly shaped and with grayed-purple 186-A overlays. In addition stems are typically colored green 138-A in combination with gray-purple 186-A.

'Chequers', similar in flower color but significantly different with smaller leaves ¾ inch long by ¾ inch wide that are centered gray-green 193-D with a broad ⅜ inch wide dark green 137-A margin.

'Pink Pewter' which displays light pink flowers 73-D and foliage smaller, to 1⅛ inch long and 1 inch wide, colored silvery 192-B with thin 1/16 inch wide green 136-B margin.

'Shell Pink', with ¾ inch long flowers that are colored pink 62-C, and leaves smaller, to 1 inch long and 1 inch wide, that are centered gray-green 192-A with a broad ½ inch wide margin of dark green 137-B.

'White Nancy', with white 155-D flowers measuring ¾ inch long by 7/16 inch wide, and leaves with similar variegation, size and coloring (to 'Orchid Frost').

I claim:

1. A new and distinct *Lamium maculatum* plant named 'Orchid Frost', as described and illustrated.

* * * * *